United States Patent [19]

Leitman

[11] Patent Number: 5,075,312

[45] Date of Patent: * Dec. 24, 1991

[54] NOVEL ANTI-MICTURITION COMPOSITION AND METHOD

[76] Inventor: Esther M. Leitman, 329 S. Roxbury Dr., Beverly Hills, Calif. 90212

[*] Notice: The portion of the term of this patent subsequent to Mar. 6, 2007 has been disclaimed.

[21] Appl. No.: 411,966

[22] Filed: Sep. 25, 1989

Related U.S. Application Data

[63] Continuation-in-part of Ser. No. 263,164, Oct. 27, 1988, Pat. No. 4,906,641.

[51] Int. Cl.$^5$ ............... A61K 31/505; A61K 31/435; A61K 31/44; A61K 31/41
[52] U.S. Cl. .................... 514/259; 514/277; 514/304; 514/359; 514/454; 514/554
[58] Field of Search ............ 514/304, 259, 277, 304, 514/359, 454, 554

[56] References Cited

U.S. PATENT DOCUMENTS

| | | | |
|---|---|---|---|
| 2,594,296 | 4/1952 | Dautrebande | 514/304 |
| 3,062,720 | 11/1962 | Costello | 514/304 |
| 3,063,901 | 11/1962 | O'Leary | 514/304 |
| 3,436,458 | 4/1969 | Teotino et al. | 424/265 |
| 3,923,990 | 12/1975 | Sokolovsky et al. | 514/315 |
| 4,644,003 | 2/1987 | Rzeszotarski et al. | 514/304 |
| 4,668,684 | 5/1987 | Tibes et al. | 514/277 |
| 4,720,494 | 1/1988 | Felger et al. | 514/252 |
| 4,788,063 | 11/1988 | Fisher et al. | 424/449 |
| 4,824,676 | 4/1989 | Bador | 424/449 |
| 4,906,641 | 3/1990 | Leitman | 514/304 |

OTHER PUBLICATIONS

Chemical Abstracts, vol. 89, p. 157365h (1976).
Chemical Abstracts, vol. 81, p. 86125b (1974).
Chemical Abstracts, vol. 79, p. 73603q, 73604r (1973).
Chemical Abstracts, vol. 73, p. 42210f (1971).
Chemical Abstracts, vol. 103, p. 206244m (1986).
Chemical Abstracts, vol. 98, p. 138013m (1983).
Chemical Abstracts, vol. 66, p. 62398g (1967).
Chemical Abstracts, vol. 78, p. 119448c (1973).
Boyd et al., "Chronic Atropinization and Fibrocystic Disease of the Pancrease", Canad. M.A.J., vol. 82 (1960).
Chemical Abstracts, vol. 66, p. 93930d (1967).
Boyd et al., "The Acute Toxicity of Atropine Sulfate", Canad. M.A.J., vol. 85, pp. 1241–1244 (1961).
Albanus et al., "The Fate of Atropine in the Dog", Acta Pharmacol. et Toxicol, vol. 26, 571–582 (1968).
B. Windbladh, "The Fate of Atropine in the Puppy", Acta Pharmacol. et Toxicol., vol. 32, 46–64 (1973).
Chem. Abst. 98: 138013m (1983), Sjoegren et al.
Chem. Abst. 66: 62398g (1967), Charvat et al.
Acta Pharmacol. et Toxicol, 1968, 26, 571–582, Albanus et al.

*Primary Examiner*—Frederick E. Waddell
*Assistant Examiner*—Zohreh A. Fay
*Attorney, Agent, or Firm*—Lowe, Price, LeBlanc & Becker

[57] ABSTRACT

A wafer, capsule or pill contains an antimuscarinic agent in controlled amounts for oral administration to housebreak domestic animals by preventing nighttime urination.

7 Claims, No Drawings

NOVEL ANTI-MICTURITION COMPOSITION AND METHOD

CROSS REFERENCE TO RELATED APPLICATION

This application is a continuation-in-part of Ser. No. 263,164, filed Oct. 27, 1988 now U.S. Pat. No. 4,906,641, issued Mar. 6, 1990.

FIELD OF THE INVENTION

This invention relates to a composition to assist in the training of domestic animals and more specifically relates to a composition and method for preventing or minimizing nighttime urination by young animals by administration of an atropine composition in harmless amounts.

BACKGROUND OF THE INVENTION

The training of domestic animals and especially young dogs, to achieve "housebroken" status is a universal problem. One of the particular problems associated with such training is to prevent nighttime micturition or urination. There is a clear need in the art for methods and compositions which would assist in training of the young domestic animals to minimize or totally avoid nighttime urination.

It is known in the art that anticholinerics or antimuscarinics such as atropine possess side effects including retention of urine. See U.S. Pat. No. 3,436,458 and U.S. Pat. No. 4,644,003. Further, various studies have been reported concerning testing of atropine and related compounds in various medical areas.

Chemical Abstracts, volume 89, page 157365, is an abstract on a Russian article regarding the effect of atropine and other compounds on the kidney excretion of hemocoagulating and fibrinolytic compounds in urine. In this abstract, atropine was found to stimulate urinary elimination of thromboplastic and antiheparin substances but depressed excretion of antithrombins in cats.

Chemical Abstracts, volume 81, page 86125b, is an abstract of a Netherlands article on the effect of administration of certain cholinergic drugs including atropine sulfate on water diuresis and electrolyte excretion in goats. In this study, atropine was found to prevent antidiuretic effects and increased electrolyte secretions when used as a pretreatment material.

Chemical Abstracts, volume 79, page 73604r, is an abstract of a Polish article regarding the effect of certain compounds on the secretory action of histamine-stimulated gastric mucosa in dogs. In this article, histamine caused secretion in dogs but atropine was found to inhibit this secretion.

Chemical Abstracts, volume 73, page 42210f, is directed to the inhibition of plasma antidiuretic activity subsequent to bleeding in sheep treated with atropine and other agents. In this abstract, atropine was one of several compounds studied with respect to antidiuretic activity in water loaded sheep. The study was based on the drugs ability to inhibit the increase in antidiuretic hormone.

In addition to these publications, the following publications from Chemical Abstracts describe work done in connection with atropine on humans such as the human bladder muscle. These abstracts are as follows:

Chemical Abstracts, Volume 103, page 206244M, 1986
Chemical Abstracts, Volume 98, page 138013M, 1983
Chemical Abstracts, Volume 66, page 62398G, 1967

In all of these abstracts, atropine is found to have an inhibitory effect on the human bladder.

The following patents disclose other uses of atropine and mixtures thereof:

U.S. Pat. No. 2,594,296
U.S. Pat. No. 3,063,901
U.S. Pat. No. 3,062,720
U.S. Pat. No. 3,923,990.

It is also known to administer atropine to domestic animals and particularly young dogs for various reasons. Thus, in a publication by Boyd et al, Canada M.A.J., Volume 32, page 821-824, 1960, there is described a study of chronic atropinization and fibrocystic disease of the pancreas in attempts to produce in young puppies a condition similar to fibrocystic disease of the pancreas in children. The work was performed upon puppies wherein atropine was injected subcutaneously dissolved in olive oil. In this study various measurements were made including testing of the urine in the urinary bladder. The results of the study indicated that the lethal dose of atropine was in the range of $125 \pm$mg/kg in puppies and $108 \pm 10$ mg/kg in kittens. The corresponding value for atropine sulfate was $181 \pm 12$ mg/kg in puppies. In addition, high dosage amounts caused various other medical problems. It is pointed out in Boyd et al that chronic administration of atropine produced in puppies a syndrome characterized by protracted cholinergic inhibition, stimulation followed by depression of the central nervous system, loss of weight and increasing cachexia. Impairment of several organs such as the gastrointestinal tract, pancreatic acinar glands, livers and thymus glands was also noted. The lungs showed pneumonia-like congestion and the output of respiratory tract fluid was increased. There was also a disturbance of salt and water metabolism.

In a further study by Boyd et al, Canadian M.A.J., volume 85, page 1241-1244, 1961, the acute toxicity of atropine sulfate was studied in rabbits. Various problems were encountered on administration of these relatively high dosages of atropine sulfate.

In a publication by Albanus, Acta Pharmacol, et toxicol, vol. 26, page 571-582, 1968, the fate of atropine in the dog was studied. The purpose of this study was to determine the metabolic fate of atropine in dogs. In the study atropine was administered by injection to dogs weighing between 10 and 15 kg with the injection being at the rate of 0.5 mg per kg expressed as atropine sulfate.

A similar study by Winbladh, Acta Pharmacol et toxicol, vol. 31, pages 46-64, 1973, discusses the fate of atropine in the puppy. In this study, atropine is administered by subcutaneous injection into new born, 3 and 6 week old, 3 month old and adult dogs in tritium labeled form. The purpose of this study was to determine the effect on various organs and determine the areas of the body which would bind to the atropine.

In this invention it has been discovered that antimuscarinics or anticholinerics such as atropine can be utilized in carefully controlled harmless dosage amounts to assist in training to housebroken status of young domestic animals.

SUMMARY OF THE INVENTION

It is accordingly one object of the present invention to provide an article and composition for oral administration to domestic animals to assist in achieving "housebroken" status.

A further object of the invention is to provide a composition in article manufacture form which contains an antimuscarinic or anticholineric agent such as atropine and which can be administered in carefully controlled harmless amounts to prevent or minimize nighttime urination of animals.

A further object of the present invention is to provide a solid article such as a wafer, capsule or pill for oral administration to a domestic animal to minimize or prevent urination, the wafer, capsule or pill comprising an antimuscarinic agent and a carrier or vehicle.

A still further object of the present invention is to provide a method for training a domestic animal to achieve "housebroken" status which comprises minimizing or preventing nighttime urination by administration thereto of a carefully controlled harmless amount of an antimuscarinic for a sufficient time to cause the animal to learn the absence of nighttime urination as routine procedure.

Other objects and advantages of the present invention will become apparent as the description thereof proceeds.

DESCRIPTION OF PREFERRED EMBODIMENTS

This invention is concerned with a composition and an article of manufacture for assisting in training domestic animals to achieve "housebroken" status. It is well known that one of the major problems of maintaining a domestic animal such as a young puppy or kitten is training the animal to be "housebroken" so that the animal can be kept in the home without damage to objects within the home. A primary problem with training, particularly young animals such as puppies, is to prevent urination during the nighttime hours. At present Applicant is unaware of any safe, effective and harmless material which can be used to assist in minimizing or preventing nighttime urination by young animals.

It is also well known that animals learn by routine. One of the objects of this invention is to provide a material which can be used by the owner or trainer to cause the young animal to establish a routine of withholding nighttime urination.

It has been discovered according to the present invention that oral administration of a carefully controlled and harmless amount of an antimuscarinic agent such as atropine will minimize or prevent nighttime urination by immature domestic animals such as puppies and kittens. By oral administration is meant that the antimuscarinic agent is contained in a form such as a wafer, capsule, or pill with one or more vehicles or carriers. It will of course be understood that the antimuscarinic agent can be administered orally in liquid form or solid form but the solid form is preferred.

In view of the above discussion of the various side effects known in humans and animals from injection of antimuscarinic agents, such as atropine, it is necessary that the article, such as a wafer, capsule or pill, contain a very carefully controlled amount of the atropine. According to this invention it has been discovered that the oral composition should contain from about 0.1 mg up to no more than about 1.2 mg of active agent in each article. Preferably, the oral composition will contain from about 0.2 mg up to about 0.6 mg of the antimuscarinic agent. The smaller amounts will be for smaller animals and the larger amounts will be for larger animals.

In this application, the active agent is referred to as an antimuscarinic agent or an anticholinergic agent. Antimuscarinics or anticholinergics are known in the medicinal art as drugs which block the activity resulting from acetyl choline. They may act at various sites in the nervous system. They act by inhibiting the action of acetyl choline on postgangoionic cholinergic nerves and smooth muscles producing mydrietic effects, cycloplegic effects, antispasmodic effects and antisecretory effects. The drugs of this type are widely used agents employed mainly as mydriatics, cycloplegics, antispasmodics and antiulcer effects. They produce side effects including blurred vision, constipation, dryness of the mouth and urine retention.

The present invention takes advantage of the urine retention side effect of such agents by the discovery that utilization of carefully controlled amounts for oral administration to young animals will assist in "housebreaking" the animals. As described in chapter 16 of the "Essentials of Medicinal Chemistry" by Korolkovas et al, John Wiley & Sons, New York, 1976, page 225-233, antimuscarinics include the general spasmolytic formula as follows: $R-COO-(CH_2)_n-N$ wherein R is an anionic group linked to the basic nitrogen through the COO bridge and the alkylene chain.

In this specification, the expression "antimuscarinic agent" and/or "anticholinergic agent" means any chemical agent suitable for the method of the invention which has anticholinergic activity and the effect of urine retention when used in a safe and effective manner in accordance with the compositions and methods of the invention.

Suitable antimuscarinic agents which may be used according to the present invention include atropine, preferably as atropine sulfate but including other forms including belladonna, scopolamine, methscopolamine bromide, homatropine, hyoscyamine, eucatropine, dicyclomine, cyclopentolate, glycopyrrolate, methantheline bromide, propantheline, bromide, tropicamide, as well as pharmaceutically acceptable salts, and mixtures thereof. There may also be included within the scope of the invention antimuscarinic agents or anticholinergic agents such as those disclosed in U.S. Pat. No. 4,824,676, 4,720,494, 4,668,684, and 4,788,063, the disclosures of these patents being hereby incorporated by references.

The preferred antimuscarinic agent is atropine, preferably used as atropine sulfate or other known salt form. However, other forms of atropine can be used. Atropine sulfate is a known material described, for example, in the Merck Index, 10th Edition, item 880, page 126, 1983. Mixtures such as Belladonna may also be used.

The antimuscarinic agent such as atropine sulfate is formulated into an article of manufacture such as a wafer, capsule or pill for oral administration. The wafer, capsule or pill will contain or be the carrier with which is antimuscarinic agent is mixed for administration. The carrier is material which can be safely eaten by the animal. An animal food is preferred. Preferably, the wafer, capsule or pill is in a form which can be administered at meal time or will contain as at least a portion of the solid carrier, a food material which would create a desire by the animal to ingest it. In general it has been found according to this invention that wafers, tablets and capsules may contain such materials as liver, dextrose, Brewers yeast, cellulose, lactose or any material known to be used in animal foods or in animal capsules, pills and wafers. In general the capsule, pill or wafer should contain a mixture of these materials in a total amount of about 2 to 400 mg and containing from 0.1 to 1.2 mg of antimuscarinic agent, preferably as atropine sulfate.

The wafer, capsule or pill is designed primarily for use with puppies of various sizes. The puppy should be three to four months old. A puppy younger than three months old is too young to train. It is of course to be understood that the smaller the animal the smaller the dosage of the antimuscarinic would be required. For purposes of this invention, however, it has been determined that the capsule may contain from 0.1 mg up to 1.2 mg of antimuscarinic agent for safe and effective administration. The total weight of the wafer, tablet or capsule including all ingredients should range from 50 to 500 mg.

In training the animal, it is preferable to exercise the animal prior to administration of the wafer, capsule or pill. Thereafter, the wafer, capsule or pill should be administered to the animal late in the evening so that it will be effective during the nighttime hours. In a preferred method, a puppy would be exercised 15 minutes prior to administration of the wafer or capsule at about 10 p.m., and th usually be effective to prevent night urination has also been determined that about 10 days of routine will be sufficient to housebreak or train the animal to prevent night urination so that the atropine can be withdrawn. The animal will then have established its routine and training will have been achieved.

The following examples are presented to illustrate the invention. However, it should not be considered as limited thereto. In the examples, parts are by weight unless otherwise indicated.

EXAMPLE 1

Tablets were produced containing atropine sulfate using the following formulations.

| Ingredients | Tablet A | Tablet B | Tablet C |
|---|---|---|---|
| Atropine sulfate | 0.2 mg | 0.4 mg | 0.6 mg |
| Desiccated Liver | 100.0 mg | 100.0 mg | 100.0 mg |
| Dextrose | 83.3 mg | 83.1 mg | 82.9 mg |
| Brewers yeast | 100.0 mg | 100.0 mg | 100.0 mg |
| Cellulose | 16.5 mg | 16.5 mg | 16.5 mg |
| Total | 300.0 mg | 300.0 mg | 300.0 mg |

These tablets each weighed 300 mg but contained 0.2 mg, 0.4 mg and 0.6 mg of atropine sulfate, respectively, as the effective ingredient. These tablets were used in a test for puppies with three puppies being given tablet A, tablet B and tablet C respectively and the fourth puppy being given a placebo. In these tests, each puppy was walked 15 minutes prior to administration of the tablet at 10 O'Clock at night. In each case, the puppies to whom tablet A, tablet B and tablet C had been administered exhibited substantially less nighttime urination. The puppy with the placebo tablet urinated during the nighttime.

EXAMPLE 2

In a test similar to Example 1, tablets were prepared containing higher dosage amounts, in this case 0.8 mg provided by two 0.4 mg tablets, and 1.2 mg, provided by administration of two 0.6 mg tablets. A third puppy received an identical placebo tablet without the atropine sulfate.

The results were the same as in Example 1 in that the puppies which had received the atropine sulfate exhibited substantially less nighttime urination. The puppy with the placebo tablet did urinate during the nighttime. No adverse effects were noted in the puppies to whom the atropine sulfate had been

EXAMPLE 3

The following formulations provide capsules which contain 0.2, 0.4 and 0.6 mg of atropine, respectively. The capsules can be produced using a Number 5 capsule which holds 60 mg.

| Ingredients | Capsule A | Capsule B | Capsule C |
|---|---|---|---|
| Atropine sulfate | 0.2 mg | 0.4 mg | 0.6 mg |
| Lactose | 59.8 mg | 59.6 mg | 59.4 mg |
| Total | 60.0 mg | 60.0 mg | 60.0 mg |

EXAMPLE 4

A clinical test in four puppies was carried out to establish dosages and effectiveness. In these tests, three puppies received 0.4, 0.8 and 1.2 mg of atropine sulfate in a chewable wafer and one puppy received an identical wafer as a placebo. A blind test demonstrated no dose related urine retention but showed a significant difference in urine retention for the atropine sulfate wafer versus the placebo. These dosages are consistent with literature information regarding the use of atropine in the puppy, the use of atropine in the dog, the acute toxicity of atropine sulfate, and chronic atropinization and fibrocystic disease of the pancreas as discussed above in publications on this subject. In these tests, no adverse reactions were noted during the administration of up to 1.2 mg of atropine sulfate once a day for several days.

EXAMPLE 5

Tablets are produced in accordance with Example 1 except that in place of atropine sulfate, the following antimuscarinic agents are used at the amounts indicated in Example 1:

Belladonna,
Scopalamine,
Homotropine,
Eucatropine.

When administered to puppies in the manner described in Example 1, the animals exhibit less frequent nighttime urination and become trained to "housebroken" status in a short period.

The invention has been described herein wit reference to certain preferred embodiments. However, as obvious variations thereon will become apparent to those skilled in the art, the invention is not to be considered as limited thereto.

I claim:

1. A method for training a domestic animal to prevent nighttime urination which comprises oral administration to said animal of an article of manufacture comprising a vehicle or carrier and from 0.1 to 1.2 mg. of an antimuscarinic agent at least one time per day for a sufficient period to cause the animal to adopt as routine the absence of nighttime urination.

2. A method according to claim 1, wherein the article of manufacture is a solid wafer, capsule or pill which is administered to said animal in the late evening hours for a period of several days until the absence of nighttime urination is a routine for the animal.

3. A method according to claim 2 wherein the wafer, capsule or pill contains from 0.2 to 0.8 mg. of antimuscarinic agent.

4. A method according to claim 1 wherein the article is a wafer.

5. A method according to claim 1 wherein the article is a capsule.

6. A method according to claim 1 wherein the article is a pill.

7. A method according to claim 4 wherein the wafer is in chewable form.

* * * * *